United States Patent [19]

Dajani

[11] Patent Number: 4,459,310
[45] Date of Patent: Jul. 10, 1984

[54] METHOD FOR CHOLESTEROL LOWERING

[75] Inventor: Esam Z. Dajani, Long Grove, Ill.

[73] Assignee: G.D. Searle & Co., Skokie, Ill.

[21] Appl. No.: 508,373

[22] Filed: Jun. 27, 1983

[51] Int. Cl.³ ..................... A61K 31/215; A61K 31/19
[52] U.S. Cl. ..................................... 424/305; 424/317
[58] Field of Search ................................ 424/305, 317

[56] References Cited

U.S. PATENT DOCUMENTS 4,132,738  1/1979  Kluender et al. .................. 424/305

*Primary Examiner*—Sam Rosen
*Attorney, Agent, or Firm*—John J. McDonnell

[57] ABSTRACT

This invention encompasses a new use for 16-loweralkyl-16-hydroxy prostaglandins such as misoprostol. This class of prostaglandin has been found useful in lowering cholesterol blood levels in patients with hypercholesterolemia.

3 Claims, No Drawings

METHOD FOR CHOLESTEROL LOWERING

BACKGROUND OF THE INVENTION

Prostaglandins having the structure

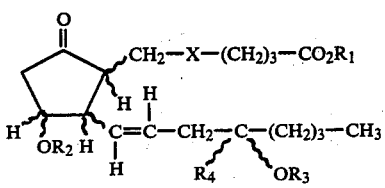

wherein $R_1$ is hydrogen or loweralkyl having 1–4 carbon atoms; $R_2$ and $R_3$ is hydrogen or loweralkanoyl being 1–4 carbon atoms $R_4$ is loweralkyl having 1–4 carbon atoms, and X is —$CH_2$—$CH_2$— or —CH═CH— are known compounds having utility in the treatment of peptic ulcer disease. The compounds, their preparation, and use in the treatment of ulcers are described in U.S. Pat. Nos. 3,965,143, 4,060,691 and 4,087,621. These patents are incorporated by reference in this specification.

Jacotot and Gero Path Biol 23 711–715 (1975) describe the effect of prostaglandin $PGE_1$ on blood and tissue lipids in rabbit experimental atherosclerosis. The 16-loweralkyl-16-hydroxy prostaglandins used in the methods of this invention lower elevated cholesterol levels to normal levels in patients with hypercholesterolemia and without effectively lowering normal cholesterol levels. Thus a new medical use of known compounds has been discovered.

DESCRIPTION OF THE INVENTION

This invention encompases a method for lowering cholesterol levels in humans comprising administering to a human having elevated cholesterol level an effective cholesterol lowering amount of a prostaglandin of the formula

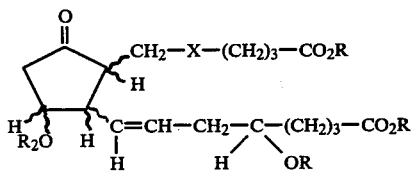

wherein $R_1$ is hydrogen or loweralkyl, $R_2$ and $R_3$ is hydrogen or loweralkanoyl and $R_4$ is loweralkyl. The preferred compounds are of the formula

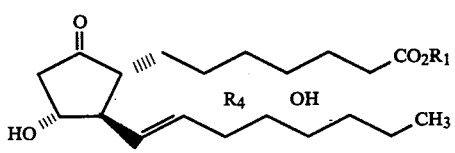

wherein $R_1$ is hydrogen or lower alkyl, and $R_4$ is loweralkyl, in particular.

methyl 7-[3(R)- hydroxy-2β-(4(RS)-4-hydroxy-4-methyl-trans-1-octenyl)-5-oxocyclopentane]-1α-heptanoate;

racemic methyl 7-[3(S)-hydroxy-2β-(4(RS)-4-hydroxy-4-methyl-1-octynyl)-5-oxocyclopentane]-1α-heptanoate;

racemic methyl 7-[3(R)-hydroxy-2β-(4-(RS)-4-cyclohexylmethyl-4-hydroxy-4-methyl-trans-1-butenyl)-5-oxocyclopentane]-1α-heptanoate;

methyl 7-[(3(R)-hydroxy-2β-(4(S)-4-hydroxy-4-methyl-trans-1-octen-1-yl)-5-oxocyclopent-1α-yl]heptanoate;

racemic methyl 7-[(3(R)-hydroxy-2β-(4(S)-4-hydroxy-r-methyl-trans-octen-1-yl)-5-oxocyclopent-1-α-yl]heptanoate;

methyl 7-[(3(R)-hydroxy-2β-(4(RS)-4-hydroxy-4-methyl-trans-1-octen-1-yl)-5-oxocyclopent-1α-yl]heptanoate;

The compounds may be combined with a variety of pharmaceutically acceptable carriers and administered in a variety of dosage forms such pill tablets and preformulated liquids as well as sustained release dosage forms. The USAN (United States Adopted Name) name misoprostol is a drug being developed for the treatment of peptic ulcer disease. Misoprostol is a 1:1 mixture of four stereoisomers shown below

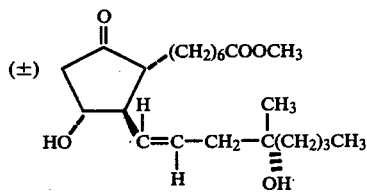

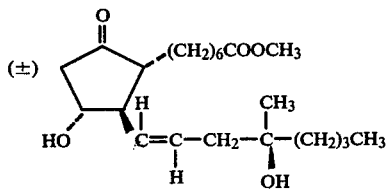

the preferred dosage is 100–200 microgram orally four times per day. Dosages from 1/10 to five (5) times the 100 microgram—four times daily dosage are effective cholesterol lowering doses.

EXAMPLE 1

Three patients with elevated cholesterol levels indicated below were given a 100 microgram of misoprostol four times daily as indicated below:

| | mg/DL cholesterol | |
|---|---|---|
| Patient | Pre-study | After-Study |
| 07(CSO) | 333 | 279 (4 Weeks) |
| 15(SH) | 353 | 268 (2 Weeks) |
| 18(FJ) | 281 | 203 (2 Weeks) | the normal range for cholesterol is 140–270 milligrams/deciliter (mg/DL).

What is claimed is:

1. A method for lowering elevated cholesterol levels in humans comprising administering to a human having elevated cholesterol an effective cholesterol lowering amount of a prostaglandin of the formula

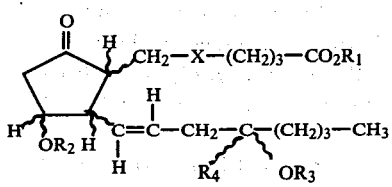

wherein $R_1$ is hydrogen or lower alkyl, $R_2$ and $R_3$ are hydrogen or loweralkanoyl, $R_4$ is lower alkyl, and x is —$CH_2$—$CH_2$— or —CH=CH—.

2. A method according to claim 1 for lowering elevated cholesterol levels in humans comprising administering to a human having elevated cholesterol an effective cholesterol lowering amount of a prostaglandin of the formula

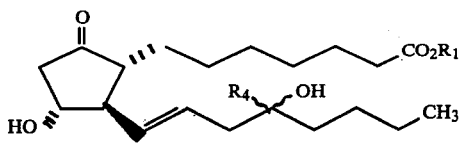

3. A method according to claim 1 for lowering elevated cholesterol levels in humans comprising administering to a human having elevated cholesterol an effective cholesterol lowering amount of misoprostol.

* * * * *